(12) United States Patent
Hoshi et al.

(10) Patent No.: US 11,406,113 B2
(45) Date of Patent: Aug. 9, 2022

(54) TIEN-CHA EXTRACT ESSENCE AND APPLICATION THEREFOR

(71) Applicant: Kabushiki Kaisha Yakult Honsha, Minato-ku (JP)

(72) Inventors: Ryotaro Hoshi, Tokyo (JP); Masatoshi Nakano, Tokyo (JP); Daisuke Nozaki, Tokyo (JP); Takao Suzuki, Shizuoka (JP)

(73) Assignee: Kabushiki Kaisha Yakult Honsha, Minato-ku (JP)

( * ) Notice: Subject to any disclaimer, the term of this patent is extended or adjusted under 35 U.S.C. 154(b) by 275 days.

(21) Appl. No.: 15/560,189

(22) PCT Filed: Mar. 22, 2016

(86) PCT No.: PCT/JP2016/058907
§ 371 (c)(1),
(2) Date: Sep. 21, 2017

(87) PCT Pub. No.: WO2016/152828
PCT Pub. Date: Sep. 29, 2016

(65) Prior Publication Data
US 2018/0077947 A1    Mar. 22, 2018

(30) Foreign Application Priority Data
Mar. 23, 2015   (JP) .............................. JP2015-059376

(51) Int. Cl.
| | | |
|---|---|---|
| A23F 3/16 | (2006.01) | |
| C12N 1/20 | (2006.01) | |
| A23L 5/20 | (2016.01) | |
| A23C 9/13 | (2006.01) | |
| A23C 9/12 | (2006.01) | |
| A23C 9/123 | (2006.01) | |
| A61K 35/745 | (2015.01) | |

(52) U.S. Cl.
CPC .............. *A23F 3/16* (2013.01); *A23C 9/1203* (2013.01); *A23C 9/1234* (2013.01); *A23C 9/13* (2013.01); *A23C 9/1307* (2013.01); *A23L 5/20* (2016.08); *A61K 35/745* (2013.01); *C12N 1/20* (2013.01); *A23C 2240/15* (2013.01); *A23V 2002/00* (2013.01); *A23V 2250/042* (2013.01); *A23Y 2300/00* (2013.01)

(58) Field of Classification Search
None
See application file for complete search history.

(56) References Cited

U.S. PATENT DOCUMENTS

| | | | |
|---|---|---|---|
| 4,288,551 A * | 9/1981 | Gudnason ............... | C13B 20/12 127/48 |
| 4,599,403 A * | 7/1986 | Kumar .................... | C07H 15/24 536/128 |
| 6,228,996 B1 * | 5/2001 | Zhou ....................... | C07G 3/00 536/128 |
| 2008/0095719 A1 * | 4/2008 | Herrmann ............... | A61P 43/00 424/48 |
| 2011/0293538 A1 | 12/2011 | Ley et al. | |
| 2012/0264831 A1 * | 10/2012 | Bridges ................... | A23L 27/10 514/777 |
| 2013/0023409 A1 * | 1/2013 | De Leij .................. | B01J 20/20 502/420 |
| 2013/0040033 A1 * | 2/2013 | Markosyan ............. | A23L 27/36 426/548 |
| 2013/0209412 A1 | 8/2013 | Hoshi et al. | |
| 2015/0056683 A1 | 2/2015 | Hoshi et al. | |
| 2015/0118379 A1 | 4/2015 | Markosyan | |

FOREIGN PATENT DOCUMENTS

| | | | | |
|---|---|---|---|---|
| CN | 102239983 A | | 11/2011 | |
| EP | 0495407 | * | 7/1992 | ............ C08B 37/00 |
| EP | 2 622 965 | | 8/2013 | |
| EP | 2 834 038 | | 3/2015 | |
| JP | 11-103817 A | | 4/1999 | |
| JP | 2002-153211 A | | 5/2002 | |
| JP | 2007-135416 A | | 6/2007 | |
| JP | 2008-43287 A | | 2/2008 | |
| JP | 2012-75382 A | | 4/2012 | |
| JP | 2013-201898 A | | 10/2013 | |
| WO | 2006/126476 A1 | | 11/2006 | |
| WO | 2006/129508 A1 | | 12/2006 | |
| WO | 2012/043532 A1 | | 4/2012 | |
| WO | 2013/146836 A1 | | 10/2013 | |

OTHER PUBLICATIONS

Ueno JP 2004166606 Derwent abstract 2 pages (Year: 2004).*
Hu et al. Derwent abstract of CN 103053689A 2013 (Year: 2013).*
Japanese Office Action dated Feb. 19, 2019 in Japanese Patent Application No. 2015-059376 (with unedited computer generated English translation), 10 pages.
Ohtani, K., et al., "Minor Diterpene Glycosides from Sweet Leaves of *Rubus suavissimus*", Phytochemistry, vol. 31 No. 5. 1992, pp. 1553-1559.
Hirono, S., et al., "Sweet and Bitter Diterpene-Glucosides from Leaves of *Rubus suavissimus*", Chemistry Pharm. Bull., vol. 38 No. 6, Jun. 1990, pp. 1743-1744.
International Search Report dated Jun. 21, 2016 in PCT/JP2016/058907 filed Mar. 22, 2016.
Extended Search Report dated Oct. 16, 2018, in European application No. 16768731.8, (7 pages).

* cited by examiner

*Primary Examiner* — Felicia C Turner
(74) *Attorney, Agent, or Firm* — Oblon, McClelland, Maier & Neustadt, L.L.P.

(57) ABSTRACT

A tien-cha extract essence characterized by being obtained by subjecting a tien-cha extract to an activated carbon treatment, and a method for producing a fermented food product using the tien-cha extract essence provide a technique which can be replaced for a tien-cha essence obtained by subjecting a tien-cha extract to electrodialysis having various problems, has no effect on flavor while maintaining the effects of the tien-cha extract of increasing the growth ability of lactic acid bacteria and the viability or the like of *bifidobacterium* bacteria, has an unprecedented effect of increasing the growth ability of *bifidobacterium* bacteria, and facilitates production and powderization.

16 Claims, No Drawings

TIEN-CHA EXTRACT ESSENCE AND APPLICATION THEREFOR

TECHNICAL FIELD

The present invention relates to a tien-cha extract essence, which can increase the growth ability of lactic acid bacteria and *bifidobacterium* bacteria and the viability of *bifidobacterium* bacteria, has no effect on flavor, and is easily produced or powdered, and application therefor.

BACKGROUND ART

Lactic acid bacteria have various effects such as improvement of intestinal flora, improvement of stool properties, improvement of intestinal function, protection from infection, immunostimulation, and prevention of cancer, and therefore have been used in production of lactic acid bacteria preparations as pharmaceutical products, and food and drink products such as fermented milks, lactic acid bacteria drinks, and cheeses. When lactic acid bacteria are used therein, lactic acid bacteria are cultured by using an animal milk as a culture medium in most cases. However, lactic acid bacteria generally have different auxotrophies depending on the species, and therefore do not grow much in a culture medium composed of only an animal milk, and even a strain having relatively excellent growth activity needs to be cultured for several days in a culture medium composed of only an animal milk in order to obtain a fermented product with a sufficient acidity when producing a fermented milk, a lactic acid bacteria drink, or the like.

However, the long-term culturing of lactic acid bacteria causes a decrease in the viable cell count, and therefore, it is not necessarily a preferred method as the culturing for producing lactic acid bacteria drinks, fermented milks, etc. which attaches importance to the viable cell count expected to have various physiological effects. Further, in order to produce various food and drink products which address the problem of the flavor of a fermented product obtained by culturing lactic acid bacteria, a strain to be used cannot be selected only from the viewpoint of growth ability, and therefore, lactic acid bacteria which produce a fermented product with good flavor are sometimes selected and used even if the bacteria have a low growth ability.

Therefore, in the culturing of lactic acid bacteria, a method in which any of various growth promoting substances is previously added to a culture medium for the purpose of improving the culture efficiency is usually used. Examples of substances which are generally regarded to be useful as growth promoting substances include a *chlorella* extract, an iron salt, vitamins, a protein hydrolysate containing amino acids or peptides, and a yeast extract. Also, the present applicant has reported a technique in which a tien-cha extract or the like is added for increasing the growth ability or the like in the culturing of lactic acid bacteria (PTL 1).

Further, *bifidobacterium* bacteria which are used in pharmaceutical products and food and drink products similarly to lactic acid bacteria are generally anaerobic bacteria, and therefore, have low viability, and quickly die particularly in the presence of oxygen.

The present applicant has reported, so far, a technique in which a tien-cha extract or the like is added to a product such as a fermented milk using *bifidobacterium* bacteria for the purpose of increasing the viability or the like of the *bifidobacterium* bacteria in the product such as a fermented milk (PTL 2).

However, the above-mentioned product such as a fermented milk to which a tien-cha extract was added had bitterness derived from tien-cha and had a problem in flavor although the growth ability or the like of lactic acid bacteria or the viability or the like of *bifidobacterium* bacteria could be increased.

Therefore, the present applicant has found, so far, a tien-cha essence obtained as a concentrate liquid by subjecting a material obtained by adding an inorganic salt such as magnesium chloride to a tien-cha extract to electrodialysis, and has reported that by culturing lactic acid bacteria in a culture medium containing the tien-cha essence, the growth of lactic acid bacteria is promoted, and also a culture which has no bitterness derived from tien-cha and has rich flavor is obtained (PTL 3). Further, the present applicant has reported that also by culturing *bifidobacterium* bacteria in a culture medium containing the tien-cha essence, the viability thereof is improved, and also a culture which has no bitterness derived from tien-cha and has rich flavor is obtained (PTL 4).

However, it was necessary to perform electrodialysis for a long time (the whole day and night) in the production of the tien-cha essence, and therefore, it took time, and a lot of electricity (energy) was needed. Further, in order to perform electrodialysis, a large amount of an inorganic salt such as magnesium chloride was added, however, there was a possibility that the inorganic salt causes precipitation of a milk component so as to cause trouble in the production of the culture. In addition, particularly, in the case where magnesium chloride was used as the inorganic salt, magnesium itself has strong bitterness, and therefore, when magnesium remained in the tien-cha essence at a high concentration, there was a possibility that the flavor of the culture is affected by the strong bitterness. Further, magnesium chloride is deliquescent, and therefore, there was a problem that when even a small amount of magnesium chloride remains in the tien-cha essence, in the case where the tien-cha essence is powdered in consideration of transportability and operability, the powder deliquesces and is liquefied after being unpacked.

CITATION LIST

Patent Literature

PTL 1: WO 2006/126476
PTL 2: WO 2006/129508
PTL 3: JP-A-2012-75382
PTL 4: JP-A-2013-201898

SUMMARY OF INVENTION

Technical Problem

Therefore, an object of the present invention is to provide a technique which can be replaced for a tien-cha essence obtained by subjecting a tien-cha extract to electrodialysis having various problems described above, has no effect on flavor while maintaining the effects of the conventional tien-cha extract or tien-cha essence of increasing the growth ability of lactic acid bacteria and the viability or the like of *bifidobacterium* bacteria, and facilitates production and powderization.

Solution to Problem

The present inventors conducted intensive studies to achieve the above-mentioned object, and as a result, they found that the object can be achieved by subjecting a tien-cha extract to an activated carbon treatment in place of electrodialysis, and thus completed the present invention.

That is, the present invention includes the following (1) to (16) inventions.

(1) A tien-cha extract essence, characterized by being obtained by subjecting a tien-cha extract to an activated carbon treatment.

(2) The tien-cha extract essence according to (1), which is a dry powder.

(3) The tien-cha extract essence according to (1) or (2), wherein the activated carbon used in the activated carbon treatment is a chemically activated carbon.

(4) The tien-cha extract essence according to any one of (1) to (3), wherein the addition amount of the activated carbon in the activated carbon treatment is 0.035 wt % or more in terms of dry weight per degree Brix of the tien-cha extract.

(5) A method for producing a tien-cha extract essence, characterized by subjecting a tien-cha extract to an activated carbon treatment.

(6) The method for producing a tien-cha extract essence according to (5), wherein the activated carbon used in the activated carbon treatment is a chemically activated carbon.

(7) The method for producing a tien-cha extract essence according to (5) or (6), wherein the addition amount of the activated carbon in the activated carbon treatment is 0.035 wt % or more in terms of dry weight per degree Brix of the tien-cha extract.

(8) A fermented food product, characterized by including a culture of lactic acid bacteria obtained by culturing the lactic acid bacteria in a culture medium in which the tien-cha extract essence according to anyone of (1) to (4) is blended.

(9) A method for producing a fermented food product, characterized by including a step of blending the tien-cha extract essence according to anyone of (1) to (4) in a culture medium before culturing lactic acid bacteria in a method for producing a fermented food product containing the lactic acid bacteria.

(10) A fermented food product, characterized by containing a culture of *bifidobacterium* bacteria obtained by culturing the *bifidobacterium* bacteria in a culture medium in which the tien-cha extract essence according to anyone of (1) to (4) is blended.

(11) A method for producing a fermented food product, characterized by including a step of blending the tien-cha extract essence according to anyone of (1) to (4) in a culture medium before culturing *bifidobacterium* bacteria in a method for producing a fermented food product containing the *bifidobacterium* bacteria.

(12) A method for promoting the growth of lactic acid bacteria and/or *bifidobacterium* bacteria, characterized by blending the tien-cha extract essence according to any one of (1) to (4) in a culture medium before culturing the lactic acid bacteria and/or the *bifidobacterium* bacteria in the culturing of the lactic acid bacteria and/or the *bifidobacterium* bacteria.

(13) An agent for promoting the growth of lactic acid bacteria and/or *bifidobacterium* bacteria, containing the tien-cha extract essence according to any one of (1) to (4) as an active ingredient.

(14) A method for improving the viability of *bifidobacterium* bacteria, characterized by blending the tien-cha extract essence according to any one of (1) to (4) in a culture medium before culturing the *bifidobacterium* bacteria in the culturing of the *bifidobacterium* bacteria.

(15) An agent for improving the viability of *bifidobacterium* bacteria, containing the tien-cha extract essence according to any one of (1) to (4) as an active ingredient.

(16) A method for improving the flavor of a tien-cha extract, characterized by subjecting the tien-cha extract to an activated carbon treatment.

Advantageous Effects of Invention

The tien-cha extract essence of the present invention has no effect on flavor while maintaining the effects of the conventional tien-cha extract or tien-cha essence of increasing the growth ability of lactic acid bacteria and the high viability of *bifidobacterium* bacteria. Further, it also has an unprecedented effect of increasing the growth ability of *bifidobacterium* bacteria. Further, the conventional tien-cha essence requires electrodialysis for the whole day and night for its production, however, for the tien-cha extract essence of the present invention, an activated carbon treatment which requires only about 30 minutes to 2 hours is performed in place of electrodialysis, and therefore, it saves energy. Further, for the tien-cha extract essence of the present invention, an inorganic salt such as magnesium chloride is not added, and therefore, even if it is used in a fermented food product, a problem of precipitation of milk does not occur. Moreover, even if the tien-cha extract essence of the present invention is powdered, a problem that the powder deliquesces and is liquefied does not occur, and thus, a powder product having excellent transportability and operability can be stably stored for a long period of time.

Accordingly, the tien-cha extract essence of the present invention can be favorably used in production of a fermented food product containing lactic acid bacteria or *bifidobacterium* bacteria.

DESCRIPTION OF EMBODIMENTS

The tien-cha extract essence of the present invention is obtained by subjecting a tien-cha extract to an activated carbon treatment.

The tien-cha extract is not particularly limited as long as it is a material obtained by solvent extraction from any portion of tien-cha (scientific name: *Rubus suavissimus* S. Lee (Rosaceae)) of the genus *Rubus* in the family Rosaceae, and examples thereof include a material obtained by subjecting leaves or stems, preferably leaves of tien-cha to solvent extraction directly or after performing a treatment such as washing, peeling, drying, or crushing as needed.

The solvent used in the production of the tien-cha extract is not particularly limited, however, examples thereof include water and organic solvents such as C1-C5 lower alcohols such as ethanol, ethyl acetate, glycerin, and propylene glycol, and among these, one type may be used alone or two or more types may be used in combination. Among these solvents, particularly, water or an aqueous solvent such as water/a lower alcohol is preferred.

Further, an extraction method for the tien-cha extract using the above-mentioned solvent is not particularly limited, however, for example, an acid extraction method is preferred. Further, this acid extraction is performed under an acidic condition of a pH of 4.0 or less, preferably a pH of 3.0 to 4.0. As an acid component used for adjusting the pH of the solvent when performing this acid extraction, any acidic substance can be used without particular limitation, however, preferred examples thereof include organic acids such as citric acid, malic acid, tartaric acid, succinic acid, lactic acid, and acetic acid.

Further, an extraction condition for the tien-cha extract using the above-mentioned solvent is not particularly limited, however, for example, extraction is performed at a temperature of 0° C. or higher and 100° C. or lower, more preferably at a temperature of 10° C. or higher and 40° C. or lower for about 30 to 60 minutes.

The tien-cha extract essence of the present invention is obtained by subjecting the tien-cha extract to an activated carbon treatment of bringing the tien-cha extract into contact with an activated carbon. A method for bringing the tien-cha extract into contact with an activated carbon is not particularly limited, however, examples thereof include a batch system in which an activated carbon is fed in the tien-cha extract, a column system in which the tien-cha extract is allowed to pass through an activated carbon column, and a cartridge system in which the tien-cha extract is allowed to pass through an activated carbon-containing cartridge, and particularly, a batch system is preferred.

The type of the activated carbon used in the above method is not particularly limited, however, examples thereof include a chemically activated carbon obtained by chemical activation using zinc chloride, phosphoric acid, sulfuric acid, calcium chloride, sodium hydroxide, or potassium hydroxide, and a gas activated carbon activated with steam, carbon dioxide gas, oxygen gas, combustion exhaust gas, a mixed gas of these gasses, or the like. Among these activated carbons, a chemically activated carbon activated with zinc chloride or a steam activated carbon is preferred, and a chemically activated carbon activated with zinc chloride is particularly preferred. As the chemically activated carbon activated with zinc chloride, a commercially available product such as TAIKO powdered activated carbon SA1000-W65 (Futamura Chemical Co., Ltd.) can be used.

The amount of the activated carbon used in this activated carbon treatment may be appropriately determined in accordance with the concentration of the tien-cha extract (Brix) or the type of the activated carbon, however, for example, in the case of a batch system, the activated carbon is added in an amount of 0.035 wt % (hereinafter simply referred to as "%") or more, preferably 0.05% to 0.5%, more preferably 0.055% to 0.085% in terms of dry weight per degree Brix of the tien-cha extract. For example, in the case where the Brix of the tien-cha extract is 2, the activated carbon is added in an amount of 0.07% or more, preferably 0.1% to 1%, more preferably 0.11% to 0.17% in terms of dry weight, and in the case where the Brix of the tien-cha extract is 20, the activated carbon is added in an amount of 0.7% or more, preferably 1% to 10%, more preferably 1.1% to 1.7% in terms of dry weight. As for a measurement method for the Brix of the tien-cha extract, for example, the measurement can be performed using an optical refractometer (a digital refractometer such as RX-7000α (ATAGO CO., LTD.)). Further, a condition when bringing the tien-cha extract into contact with the activated carbon is not particularly limited, however, after the activated carbon is fed, stirring may be performed at room temperature for about 30 minutes to 2 hours.

Other than the above-mentioned activated carbon treatment, a treatment such as centrifugation, diatomaceous earth filtration, microfiltration, concentration, or sterilization may be performed as needed. Examples of a preferred method for producing the tien-cha extract essence of the present invention include a method in which the tien-cha extract is subjected to the activated carbon treatment, and thereafter is subjected to treatments of centrifugation, diatomaceous earth filtration, microfiltration, concentration, and sterilization in this order, or a method in which the tien-cha extract is subjected to the activated carbon treatment after being subjected to microfiltration, and thereafter is subjected to treatments of centrifugation, diatomaceous earth filtration, concentration, and sterilization in this order. A condition for the centrifugation is not particularly limited as long as it is a condition capable of removing the activated carbon, however, examples thereof include a condition in which centrifugation is performed at 10,000 g for 2 minutes. A condition for the diatomaceous earth filtration is not particularly limited, however, examples thereof include a condition in which diatomaceous earth is added in an amount of 0.1%, and thereafter, filtration is performed using a standard filter paper No. 131. A condition for the microfiltration is not particularly limited, however, examples thereof include a condition in which filtration is performed using a 0.2 μm microfilter. Examples of a condition for the concentration include a condition in which concentration is performed using an evaporator or the like until the Brix reaches a desired value. Further, a condition for the sterilization is also not particularly limited, however, examples thereof include a condition in which after the temperature reaches 90° C., cooling is performed to 50° C. or lower.

The thus obtained tien-cha extract essence is preferably changed into a dry powder from the viewpoint of handleability. Incidentally, this dry powder does not contain magnesium chloride, and therefore is not deliquescent and can be stably stored. Further, it is possible to confirm that the dry powder is not deliquescent by the method described in Examples.

A method for obtaining the above-mentioned dry powder is not particularly limited, and examples thereof include spray drying and freeze drying, however, a method of obtaining the dry powder by spray drying is preferred. A drying condition for spray drying is not particularly limited, however, examples thereof include a condition in which the inlet temperature is 160° C., the outlet temperature is 80 to 100° C., and the flow rate is 10 mL/min. Further, in the case where drying is performed by spray drying, an excipient may be added as needed. Examples of the excipient include dextrin, cyclodextrin, starch, and maltose, however, dextrin is particularly preferred. The addition amount of the excipient is not particularly limited, however, for example, in the case where dextrin is used as the excipient, dextrin is added at a weight ratio of 0.5 to 5, preferably at a weight ratio of 1 to 2, more preferably at a weight ratio of 1.5 with respect to the solid content of the tien-cha extract essence, which is taken as 1.

By blending the tien-cha extract essence of the present invention in a culture medium and culturing lactic acid bacteria therein, a culture of lactic acid bacteria is obtained, and a fermented food product containing the culture of lactic acid bacteria can be obtained. Examples of the culture medium in which the tien-cha extract essence of the present invention is blended and lactic acid bacteria are cultured include an animal milk culture medium composed of a raw milk such as cow milk, goat milk, horse milk, or sheep milk, a dairy product such as powdered skim milk, powdered whole milk, or fresh cream, or the like, a liquid milk derived from a vegetable such as soybean milk, and various synthetic culture media. To such a culture medium, a component which is used in a common culture medium for lactic acid bacteria may be added. Examples of such a component include saccharides such as glucose, vitamins such as vitamin A, B vitamins, vitamin C, and vitamin E, various peptides, amino acids, and salts of calcium, magnesium, and the like.

Further, oleic acids may be added to the above-mentioned culture medium. Examples of the oleic acids include oleic acid, salts of oleic acid such as sodium oleate and potassium oleate, and derivatives of oleic acid esters such as glycerin oleic acid esters, polyglycerin oleic acid esters, and sucrose oleic acid esters. Such an oleic acid may be added to the culture medium at a concentration of about 5 to 50 ppm, preferably 5 to 25 ppm in terms of oleic acid.

The lactic acid bacteria cultured in the culture medium in which the tien-cha extract essence of the present invention is blended are not particularly limited as long as they are lactic acid bacteria generally used in production of food products, however, examples thereof include *Lactobacillus* bacteria such as *Lactobacillus casei, Lactobacillus gasseri, Lactobacillus acidophilus, Lactobacillus cremoris, Lactobacillus helveticus, Lactobacillus salivarius, Lactobacillus fermentum, Lactobacillus yoghurti, Lactobacillus delbrueckii* subsp. *bulgaricus, Lactobacillus delbrueckii* subsp. *delbrueckii*, and *Lactobacillus johnsonii, Streptococcus* bacteria such as *Streptococcus thermophiles, Lactococcus* bacteria such as *Lactococcus lactis* subsp. *lactis, Lactococcus lactis* subsp. *cremoris, Lactococcus plantarum*, and *Lactococcus raffinolactis*, and *Enterococcus* bacteria such as *Enterococcus faecalis* and *Enterococcus faecium*. Among these lactic acid bacteria, *Lactobacillus* bacteria, *Streptococcus* bacteria, and *Lactococcus* bacteria are preferred, and among them, *Lactobacillus casei, Lactobacillus gasseri, Lactococcus lactis*, and *Streptococcus* thermophiles are preferred, and particularly *Lactobacillus casei* YIT9029 (FERN BP-1366, date of deposit: Jan. 12, 1981), *Lactobacillus gasseri* YIT0192 (DSM20243), *Lactococcus lactis* YIT2027 (FERN BP-6224, date of deposit: Feb. 10, 1997), and *Streptococcus thermophiles* YIT2021 (FERM BP-7537, date of deposit: Nov. 1, 1996) are preferred. As the lactic acid bacteria, one species, or two or more species may be used, and also, the lactic acid bacteria may be used in combination with one species, or two or more species of the below-mentioned *bifidobacterium* bacteria.

The blending amount of the tien-cha extract essence of the present invention in the culture medium when culturing the lactic acid bacteria is not particularly limited, however, the blending amount in terms of tien-cha extract essence dry powder (in terms of dry powder which does not contain the excipient and contains only the tien-cha extract essence) is, for example, from 0.0004% to 0.12% (from 0.0035% to 1% in terms of tien-cha extract essence having a Brix of 11.5), preferably from 0.0012% to 0.012% (from 0.01% to 0.1% in terms of tien-cha extract essence having a Brix of 11.5).

Further, a culturing condition for obtaining the culture of lactic acid bacteria is not particularly limited, however, examples thereof include a condition in which the lactic acid bacteria are inoculated into the culture medium so that the cell count in the culture medium is about $1.0 \times 10^3$ to $1.0 \times 10^9$ cfu/mL, and cultured at a temperature of about 30 to 40° C. for 1 to 7 days. As for the culturing condition at this time, a method suitable for culturing the lactic acid bacteria to be used may be appropriately selected from static culturing, stirring culturing, shaking culturing, aeration culturing, and the like, and performed.

The fermented food product containing the culture of lactic acid bacteria obtained by blending the tien-cha extract essence of the present invention in the culture medium and culturing the lactic acid bacteria therein can be produced according to a conventionally known method for producing a fermented food product except that the tien-cha extract essence is blended in the culture medium before culturing the lactic acid bacteria. Here, the fermented food product containing the culture of lactic acid bacteria includes, for example, fermented milks specified by the ministerial ordinance such as fermented soybean milks or milks, dairy product lactic acid bacteria drinks, lactic acid bacteria drinks, and the like. Further, the above-mentioned fermented food product includes various food and drink products using lactic acid bacteria, for example, fermented milks such as plain type, flavored type, fruit type, sweet type, soft type, drink type, solid (hard) type, and frozen type, lactic acid bacteria drinks, kefir, and the like.

Further, the fermented food product containing the culture of lactic acid bacteria is obtained by blending a sweetener such as syrup, and other various food materials, for example, arbitrary components such as various carbohydrates, a thickener, an emulsifier, and various vitamins as needed. Specific examples of the food materials include carbohydrates such as sucrose, glucose, fructose, palatinose, trehalose, lactose, xylose, and maltose, sugar alcohols such as sorbitol, xylitol, erythritol, lactitol, palatinit, reduced starch syrup, and reduced maltose syrup, high intensity sweeteners such as aspartame, thaumatin, sucralose, acesulfame K, and *stevia*, various thickeners (stabilizers) such as agar, gelatin, carrageenan, Guar gum, xanthan gum, pectin, locust bean gum, gellan gum, carboxymethyl cellulose, soybean polysaccharides, and propylene glycol alginate, emulsifiers such as sucrose fatty acid esters, glycerin fatty acid esters, polyglycerin fatty acid esters, sorbitan fatty acid esters, and lecithin, milk fats such as cream, butter, and sour cream, acidulants such as citric acid, lactic acid, acetic acid, malic acid, tartaric acid, and gluconic acid, various vitamins such as vitamin A, B vitamins, vitamin C, and E vitamins, minerals such as calcium, magnesium, zinc, iron, and manganese, and flavors such as yogurt-type, berry-type, orange-type, quince-type, *perilla*-type, citrus-type, apple-type, mint-type, grape-type, apricot-type, pear-type, custard cream-type, peach-type, melon-type, banana-type, tropical-type, herb-type, black tea-type, and coffee-type flavors.

By blending the tien-cha extract essence of the present invention in a culture medium and culturing *bifidobacterium* bacteria in the culture medium, a culture of *bifidobacterium* bacteria is obtained, and a fermented food product containing the culture of *bifidobacterium* bacteria can be obtained. Examples of the culture medium in which the tien-cha extract essence of the present invention is blended and *bifidobacterium* bacteria are cultured include an animal milk culture medium composed of a raw milk such as cow milk, goat milk, horse milk, or sheep milk, a dairy product such as powdered skim milk, powdered whole milk, or fresh cream, or the like, a liquid milk derived from a vegetable such as soybean milk, and various synthetic culture media similarly to the culture medium in which lactic acid bacteria are cultured as described previously. To such a culture medium, a component which is used in a common culture medium for *bifidobacterium* bacteria may be added. Examples of such a component include saccharides such as glucose, vitamins such as vitamin A, B vitamins, vitamin C, and vitamin E, various peptides, amino acids, and salts of calcium, magnesium, and the like.

Further, similarly to the culture medium in which lactic acid bacteria are cultured, the oleic acids described above may be added to the culture medium in which *bifidobacterium* bacteria are cultured, and also as for the addition amount thereof, in the same manner as described previously, it may be added to the culture medium at a concentration of about 5 to 50 ppm, preferably 5 to 25 ppm in terms of oleic acid.

The *bifidobacterium* bacteria cultured in the culture medium in which the tien-cha extract essence of the present invention is blended are not particularly limited, however, examples thereof include *Bifidobacterium breve, Bifidobacterium bifidum, Bifidobacterium longum, Bifidobacterium infantis, Bifidobacterium adolescentis, Bifidobacterium catenulatum, Bifidobacterium pseudocatenulatum, Bifidobacterium angulatum, Bifidobacterium gallicum, Bifidobacterium lactis*, and *Bifidobacterium animalis*. Among these *bifidobacterium* bacteria, *Bifidobacterium breve, Bifidobacterium bifidum*, and *Bifidobacterium longum* are preferred, and particularly, *Bifidobacterium breve* YIT12272 (FERM BP-11320, date of deposit: Feb. 16, 2010) and *Bifidobacterium bifidum* YIT10347 (FERM BP-10613, date of deposit: Jun. 23, 2005) are preferred. As the *bifidobacterium* bacteria, one species, or two or more species may be used, and also, the *bifidobacterium* bacteria may be used in combination with one species, or two or more species of the above-mentioned lactic acid bacteria.

The above-mentioned lactic acid bacteria and *bifidobacterium* bacteria for which the date of deposit is described were all deposited at the International Patent Organism Depositary, the National Institute of Technology and Evaluation (#120, 2-5-8 Kazusakamatari, Kisarazu-shi, Chiba, 292-0818, Japan).

The blending amount of the tien-cha extract essence of the present invention when culturing the *bifidobacterium* bacteria is not particularly limited, however, for example, in the case where the growth ability of the *bifidobacterium* bacteria is desired to be increased, the blending amount thereof in terms of tien-cha extract essence having a Brix of 11.5 is from 0.001% to 1%, preferably from 0.35% to 0.55%. Further, in the case where the viability of the *bifidobacterium* bacteria is desired to be maintained at a high level, the blending amount thereof in terms of tien-cha extract essence dry powder (in terms of dry powder which does not contain the excipient and contains only the tien-cha extract essence) is from 0.0004% to 0.12% (from 0.0035% to 1% in terms of tien-cha extract essence having a Brix of 11.5), preferably from 0.0012% to 0.012% (from 0.01% to 0.1% in terms of tien-cha extract essence having a Brix of 11.5).

Further, a culturing condition for obtaining the culture of *bifidobacterium* bacteria is not particularly limited, however, examples thereof include a condition in which the *bifidobacterium* bacteria are inoculated into the culture medium so that the cell count in the culture medium is about $1.0 \times 10^3$ to $1.0 \times 10^9$ cfu/mL, and cultured at a temperature of about 30 to 40° C. for 12 hours to 7 days or until the pH reaches about 4 to 5.5. As for the culturing condition at this time, a method suitable for culturing the *bifidobacterium* bacteria to be used may be appropriately selected from static culturing, stirring culturing, shaking culturing, and the like, and performed, however, the culturing is preferably performed under an anaerobic condition.

The fermented food product containing the culture of *bifidobacterium* bacteria obtained by blending the tien-cha extract essence of the present invention in the culture medium and culturing the *bifidobacterium* bacteria therein can be produced according to a conventionally known method for producing a fermented food product except that the tien-cha extract essence is blended in the culture medium before culturing the *bifidobacterium* bacteria. The fermented food product containing the culture of *bifidobacterium* bacteria includes, for example, fermented milks specified by the ministerial ordinance such as fermented soybean milks or milks, dairy product lactic acid bacteria drinks, lactic acid bacteria drinks, and the like, and includes various food and drink products using *bifidobacterium* bacteria similarly to the fermented food product containing the culture of lactic acid bacteria as described above. Further, the above-mentioned fermented food product is obtained by blending a sweetener or other various food materials as described previously and similar to the fermented food product containing the culture of lactic acid bacteria.

In the thus obtained fermented food product containing the culture of lactic acid bacteria obtained by blending the tien-cha extract essence of the present invention, the growth ability of the lactic acid bacteria is improved, and also, in the fermented food product containing the culture of *bifidobacterium* bacteria obtained by blending the tien-cha extract essence of the present invention, the growth ability and viability of the *bifidobacterium* bacteria are improved. Moreover, these fermented food products do not have bitterness derived from tien-cha and have a favorable flavor. Therefore, these fermented food products have high usefulness, and are useful in promoting health. Incidentally, the viability can be obtained by the method described in Examples.

EXAMPLES

Hereinafter, the present invention will be described in detail with reference to Examples. However, the present invention is by no means limited to these Examples.

Reference Example 1

Production of Tien-Cha Extract 1

Leaves of tien-cha (scientific name: *Rubus suavissimus* S. Lee (Rosaceae)) were subjected to a crushing treatment, and then, water in an amount 15 times the amount of the leaves of tien-cha and citric acid in an amount corresponding to 5% of the leaves of tien-cha were added thereto to adjust the pH to 3.8, and the mixture was stirred at 25° C. for 60 minutes to effect extraction, whereby a tien-cha extract having a Brix of 2.0 was obtained. Further, the obtained tien-cha extract having a Brix of 2.0 was concentrated to about 10.3 times using an evaporator, whereby a tien-cha extract having a Brix of 20.6 was obtained.

Example 1

Production of Tien-Cha Extract Essence Dry Powder
(1) Selection of Activated Carbon Rubusoside and polyphenols remaining in the tien-cha extract, and a high Brix value of the tien-cha extract has an effect on the flavor of a fermented food product, and therefore, the amounts of these substances when using each activated carbon were measured.

To the tien-cha extract having a Brix of 20.6 produced in Reference Example 1, each activated carbon of a type shown in Table 1 was added in an addition amount shown in Table 1, followed by stirring for 30 minutes, and the Brix of the resulting solution was measured using a digital refractometer RX-7000α (ATAGO CO., LTD.). Further, rubusoside contained in the solution was measured by the HPLC method. The HPLC method was performed under the following condition.

Device: waters alliance 2690
Detector: PDA detector W2996
Measurement wavelength: 210 nm
Column: YMC-Pack ODS-A 150×4.6 mm I.D. S-5 μm
Column temperature: 25° C.

Mobile phase: line A (a 0.17% aqueous phosphoric acid solution), line B (0.17% phosphoric acid/acetonitrile)

Liquid feeding condition: flow rate 1.0 mL/min gradient elution gradient condition:

| (Time) | (line A) | (line B) |
|---|---|---|
| 0 → 5 min (fixed composition) | 75% | 25% |
| 5 → 30 min (linear gradient) | 30% | 70% |

The amount of polyphenols contained in the solution was measured by the ferrous tartrate method. Further, the amount of polyphenols was calculated in terms of ethyl gallate. Further, the results of the Brix, and the contents of rubusoside and polyphenols when using each activated carbon are shown in Table 1.

TABLE 1

| Type of activated carbon | Addition amount (%) | Brix | Rubusoside (mg/ml) | Polyphenols (mg %) |
|---|---|---|---|---|
| without addition | 0 | 20.6 | 15.15 | 1106 |
| Chemically activated carbon A*[1] | 1.13 | 18.9 | 10.55 | 911 |
|  | 1.51 | 18.3 | 8.88 | 836 |
| Steam activated carbon A*[2] | 2.15 | 19.2 | 11.74 | 968 |
|  | 4.30 | 17.7 | 7.81 | 774 |
| Steam activated carbon B*[3] | 2.15 | 19.8 | 14.41 | 1050 |
|  | 4.30 | 19.1 | 13.42 | 976 |

*[1]TAIKO powdered activated carbon SA1000-W65 (Futamura Chemical Co., Ltd.) This product contains water at 65%, however, the addition amount shown in Table 1 is the amount in terms of dry weight without water.
*[2]TAIKO powdered activated carbon K (Dry) (Futamura Chemical Co., Ltd.)
*[3]TAIKO powdered activated carbon M (W50) (Futamura Chemical Co., Ltd.) This product contains water at 50%, however, the addition amount shown in Table 1 is the amount in terms of dry weight without water.

As a result, in the case where an activated carbon was not added, the Brix was the highest, and also the residual amounts of rubusoside and polyphenols were the largest. By using the chemically activated carbon and the steam activated carbon, the Brix and also the amounts of rubusoside and polyphenols were decreased, however, particularly, in the case where the chemically activated carbon was added, although the addition amount thereof was smaller than that of the steam activated carbon, the Brix and the contents of rubusoside and polyphenols were further decreased as compared with the case where the steam activated carbon was added.

In the case where the amount of the activated carbon is large, as compared with the case where the amount thereof is small, the time required for a step of removing the activated carbon is long, and therefore, an activated carbon capable of reducing the amounts of these substances with a small addition amount is preferred, and thus, it was found that as the activated carbon, the chemically activated carbon activated by zinc chloride is more favorable than the steam activated carbon.

(2) Production of Tien-Cha Extract Essence

To the tien-cha extract having a Brix of 2.0 produced in Reference Example 1, a chemically activated carbon (TAIKO powdered activated carbon SA1000-W65 (Futamura Chemical Co., Ltd.)) was added in an amount of 0.14% (in terms of dry weight), followed by stirring for 30 minutes. After stirring, the resulting mixture was centrifuged at 10,000×g for 2 minutes. The supernatant was subjected to diatomaceous earth filtration (diatomaceous earth (manufactured by Tokyo Konno Co., Ltd.) was added in an amount of 0.1%, and thereafter, filtration was performed using a filter paper No. 131). The solution obtained after diatomaceous earth filtration was subjected to microfiltration using a 0.2 μm microfilter (manufactured by Toyo Roshi Kaisha, Ltd.), and the filtrate was concentrated using an evaporator until the Brix reached 11.5. After concentration, the temperature was increased to 90° C. to effect sterilization, followed by cooling to 50° C. or lower, whereby a tien-cha extract essence was obtained.

(3) Powderization of Tien-Cha Extract Essence

Dextrin (manufactured by Cargill Japan) was added at a weight ratio of 60 with respect to 40 of the solid content of the tien-cha extract essence obtained in (2), and water was mixed therein to dissolve the components, and the resulting solution was powdered using a spray dryer (manufactured by Nihon Buchi). The powderization was performed under a powderization condition that the inlet temperature was 160° C., the outlet temperature was 80 to 100° C., and the flow rate was 10 mL/min.

It could be confirmed by visual observation that even when being left at room temperature for 2 hours, the obtained tien-cha extract essence dry powder did not deliquesce.

Example 2

Production of Fermented Food Product Containing Lactic Acid Bacteria

A 10% powdered skim milk solution was used as a basal culture medium, and the tien-cha extract essence dry powder produced in Example 1 was added to the basal culture medium in an amount shown in Table 2. Into this culture medium, a starter of *Lactobacillus casei* YIT9029 was inoculated in an amount of 0.1% (initial cell count: $1.5 \times 10^6$ cfu/mL), and culturing was performed at 37° C. for 24 hours to obtain a culture of lactic acid bacteria, followed by cooling to 10° C. or lower, whereby a fermented milk was obtained. The pH and acidity of this fermented milk and the viable cell count therein were measured. The pH was measured using a pH meter (HORIBA F-52). The acidity was determined by taking 9 g of the fermented milk, and measuring the titration value (unit: mL) when neutralization titration was performed with 0.1 N sodium hydroxide until the pH reached 8.5. Further, the viable cell count was measured using a BCP medium (manufactured by Eiken Chemical Co., Ltd.). In addition, the flavor of the obtained fermented milk was evaluated by three expert panelists according to the following evaluation criteria. The results are shown in Table 2.

TABLE 2

|  | Addition amount of tien-cha extract essence dry powder (%)* | pH of fermented milk | Acidity of fermented milk | Viable cell count in fermented milk (cfu/ml) | Flavor |
|---|---|---|---|---|---|
| Basal culture medium | 0 (0) | 5.42 | 4.2 | $4.4 \times 10^8$ | — |
| Culture medium 1 | 0.0004 (0.001) | 5.07 | 6.7 | $9.3 \times 10^8$ | 5 |
| Culture medium 2 | 0.0012 (0.003) | 4.73 | 8.2 | $3.8 \times 10^9$ | 5 |

TABLE 2-continued

|  | Addition amount of tien-cha extract essence dry powder (%)* | pH of fermented milk | Acidity of fermented milk | Viable cell count in fermented milk (cfu/ml) | Flavor |
|---|---|---|---|---|---|
| Culture medium 3 | 0.004 (0.01) | 4.46 | 9.9 | $6.7 \times 10^9$ | 5 |
| Culture medium 4 | 0.012 (0.03) | 4.30 | 11.5 | $7.4 \times 10^9$ | 5 |
| Culture medium 5 | 0.04 (0.1) | 4.27 | 11.9 | $7.1 \times 10^9$ | 4 |
| Culture medium 6 | 0.12 (0.3) | 4.27 | 11.8 | $7.9 \times 10^9$ | 3 |

*It shows the amount in terms of dry powder which does not contain dextrin and contains only the tien-cha extract essence dry powder. The number in the parentheses indicates the addition amount of a dry powder obtained by powderization after dextrin was added at a weight ratio of 60 with respect to 40 of the solid content of the tien-cha extract essence.

<Evaluation Criteria for Flavor>
Evaluation: Contents
5: Bitterness and astringency are not felt at all.
4: Bitterness and astringency are almost not felt.
3: Bitterness and astringency are slightly felt.
2: Bitterness and astringency are felt.
1: Bitterness and astringency are strongly felt.

The fermented milk containing the culture of lactic acid bacteria obtained by culturing in the culture medium to which the tien-cha extract essence dry powder (the dry powder which does not contain dextrin and contains only the tien-cha extract essence dry powder) was added in an amount of 0.0004% or more (0.0035% or more in terms of tien-cha extract essence having a Brix of 11.5) showed the results that the culturing of *Lactobacillus casei* was promoted, and the viable cell count was high ($5.0 \times 10^8$ cfu/mL or more) as compared with the fermented milk obtained without adding the tien-cha extract essence dry powder. The promotion of culturing of *Lactobacillus casei* was confirmed by also the degree of decrease in the pH and the increase in the acidity.

In particular, in the case where the tien-cha extract essence dry powder (the dry powder which does not contain dextrin and contains only the tien-cha extract essence dry powder) was added in an amount of 0.0012% to 0.012% (0.01% to 0.1% in terms of tien-cha extract essence having a Brix of 11.5), the effect of promoting the culturing of *Lactobacillus casei* was remarkable, and also the flavor was favorable.

Example 3

Production of Fermented Food Product Containing *Bifidobacterium* Bacteria (1)

A 20% powdered skim milk solution was used as a basal culture medium, and the tien-cha extract essence dry powder produced in Example 1 was added to the basal culture medium in an amount shown in Table 3. Into this culture medium, a starter of *Bifidobacterium breve* YIT12272 was inoculated in an amount of 1% (initial cell count: $1.0 \times 10^7$ cfu/mL), and culturing was performed at 37° C. for 24 hours, whereby a fermented milk was obtained. This fermented milk was packed in a glass container, and the container was tightly sealed with a butyl stopper and stored at 10° C. for 21 days. The viable cell count before and after storage was measured using a TOS medium (manufactured by Yakult Pharmaceutical Industry Co., Ltd.). Further, the flavor after storage was evaluated in the same manner as in Example 2. In addition, from the viable cell count before and after storage, the viability ((viable cell count after storage)/viable cell count at production)×100(%)) was obtained. These results are shown in Table 3.

TABLE 3

|  | Addition amount of tien-cha extract essence dry powder (%)* | Viable cell count at production (cfu/mL) | Viable cell count after storage (cfu/mL) | Viability | Flavor |
|---|---|---|---|---|---|
| Basal culture medium | 0 (0) | $1.1 \times 10^9$ | $2.1 \times 10^8$ | 19 | — |
| Culture medium 1 | 0.0004 (0.001) | $1.0 \times 10^9$ | $2.3 \times 10^8$ | 23 | 5 |
| Culture medium 2 | 0.0012 (0.003) | $1.1 \times 10^9$ | $2.8 \times 10^8$ | 25 | 5 |
| Culture medium 3 | 0.004 (0.01) | $1.2 \times 10^9$ | $3.4 \times 10^8$ | 28 | 5 |
| Culture medium 4 | 0.012 (0.03) | $1.2 \times 10^9$ | $3.9 \times 10^8$ | 33 | 5 |
| Culture medium 5 | 0.04 (0.1) | $1.2 \times 10^9$ | $3.3 \times 10^8$ | 28 | 4 |
| Culture medium 6 | 0.12 (0.3) | $1.1 \times 10^9$ | $3.6 \times 10^8$ | 33 | 3 |

*It shows the amount in terms of dry powder which does not contain dextrin and contains only the tien-cha extract essence dry powder. The number in the parentheses indicates the addition amount of a dry powder obtained by powderization after dextrin was added at a weight ratio of 60 with respect to 40 of the solid content of the tien-cha extract essence.

In the fermented milk containing the culture of *bifidobacterium* bacteria obtained by culturing *Bifidobacterium breve* in the culture medium to which the tien-cha extract essence dry powder (the dry powder which does not contain dextrin and contains only the tien-cha extract essence dry powder) was added in an amount of 0.0004% or more (0.0035% or more in terms of tien-cha extract essence having a Brix of 11.5), the viability of *Bifidobacterium breve* was improved as compared with the fermented milk obtained without adding the tien-cha extract essence dry powder.

In particular, in the case where the tien-cha extract essence dry powder (the dry powder which does not contain dextrin and contains only the tien-cha extract essence dry powder) was added in an amount of 0.0012% to 0.012% (0.01% to 0.1% in terms of tien-cha extract essence having a Brix of 11-5), the effect of improving the viability of *Bifidobacterium breve* was remarkable, and also the flavor was favorable.

Example 4

Production of Fermented Food Product Containing *Bifidobacterium* Bacteria (2)

An 18% powdered milk solution (or a powdered milk solution containing 14% solids-not-fat (SNF)) was used as a basal culture medium, and a culture medium in which the tien-cha extract essence having a Brix of 11.5 produced in Example 1 (2) was added in an amount of 0.44% to the basal culture medium, and a culture medium in which the tien-cha extract essence was not added were prepared. To each of these culture media, a whey peptide (LE80GF-US) was added, and then, a starter of *Bifidobacterium bifidum* YIT10347 was inoculated therein in an amount of 3% (initial cell count: $2.8 \times 10^7$ cfu/mL), and culturing was performed at 37° C. until the pH reached 4.9. Thereafter, the culture solution was cooled to 10° C. or lower, whereby a fermented milk was obtained. The viable cell count in this fermented milk was measured. The results are shown in Table 4.

TABLE 4

| pH of fermented milk | Addition amount of tien-cha extract essence (%) | Culturing time (h) | Viable cell count in fermented milk (cfu/ml) |
|---|---|---|---|
| 4.9 | 0 | 28.0 | $4.4 \times 10^9$ |
|  | 0.44 | 20.5 | $5.6 \times 10^9$ |

In the case of the fermented milk obtained by culturing *Bifidobacterium bifidum* in the culture medium to which the tien-cha extract essence having a Brix of 11.5 was added in an amount of 0.44%, as compared with the fermented milk obtained without adding the tien-cha extract essence, the culturing time was short, and the viable cell count in the fermented milk tended to be high although the pH and the condition of the added whey peptide were the same.

It has been known that the tien-cha extract has an effect of slightly reducing the culturing time of *Bifidobacterium bifidum* (an effect of reducing the culturing time to about 92%) (PTL 2). However, by adding the tien-cha extract essence in an amount of 0.44%, the culturing time of *Bifidobacterium bifidum* YIT10347 could be reduced to about 73%, and therefore, an effect of promoting the growth was confirmed. Accordingly, although the reason has not yet been made clear, it was revealed that by subjecting the tien-cha extract to the activated carbon treatment, the effect of promoting the growth of *Bifidobacterium bifidum* becomes remarkable.

Example 5

Production of Tien-Cha Extract Essence Dry Powders A and B
(1) Production of Tien-Cha Extract Essence A The tien-cha extract having a Brix of 2.0 produced in Reference Example 1 was subjected to microfiltration using a 0.2 μm microfilter (manufactured by Toyo Roshi Kaisha, Ltd.), and to the obtained solution, a chemically activated carbon (TAIKO powdered activated carbon SA1000-W65 (Futamura Chemical Co., Ltd.)) was added in an amount of 0.14% (in terms of dry weight), followed by stirring for 30 minutes. After stirring, the resulting mixture was centrifuged at 10,000×g for 2 minutes. The supernatant was subjected to diatomaceous earth filtration (diatomaceous earth (manufactured by Tokyo Konno Co., Ltd.) was added in an amount of 0.1%, and thereafter, filtration was performed using a filter paper No. 131). The obtained solution was concentrated using an evaporator until the Brix reached 11.5. After concentration, the temperature was increased to 90° C. to effect sterilization, followed by cooling to 50° C. or lower, whereby a tien-cha extract essence A was obtained.

Dextrin (manufactured by Cargill Japan) was added at a weight ratio of 60 with respect to 40 of the solid content of the tien-cha extract essence A obtained above, and water was mixed therein to dissolve the components, and the resulting solution was powdered using a spray dryer (manufactured by Nihon Buchi). The powderization was performed under the same powderization condition as in Example 1(3). The obtained powder was named "tien-cha extract essence dry powder A".

It could be confirmed by visual observation that even when being left at room temperature for 2 hours, the tien-cha extract essence dry powder A did not deliquesce.
(2) Production of Tien-Cha Extract Essence Dry Powder B A tien-cha extract essence dry powder B was produced in the same manner as in Example 1(2) and (3).

Reference Example 2

Production of Tien-Cha Extract Dry Powder and Tien-Cha Extract Electrodialysate Dry Powder
(1) Production of Tien-Cha Extract Dry Powder The tien-cha extract having a Brix of 2.0 produced in Reference Example 1 was concentrated using an evaporator until the Brix reached 11.5, and thereafter, the temperature was increased to 90° C. to effect sterilization, followed by cooling to 50° C. or lower. Dextrin (manufactured by Cargill Japan) was added at a weight ratio of 60 with respect to 40 of the solid content of the obtained tien-cha extract having a Brix of 11.5, and water was mixed therein to dissolve the components, and the resulting solution was powdered using a spray dryer (manufactured by Nihon Buchi). The powderization was performed under the same powderization condition as in Example 1(3). The obtained powder was named "tien-cha extract dry powder".

It could be confirmed by visual observation that even when being left at room temperature for 2 hours, the tien-cha extract dry powder did not deliquesce.
(2) Production of Tien-Cha Extract Electrodialysate Dry Powder The tien-cha extract having a Brix of 2.0 produced in Reference Example 1 was subjected to microfiltration using a 0.2 μM microfilter (manufactured by Toyo Roshi Kaisha, Ltd.), and to the obtained solution, magnesium chloride hexahydrate was added so that the concentration of magnesium chloride was 1%. Subsequently, the resulting mixture was placed in a desalting chamber in an electrodialyzer (electrodialytic membrane: AC220-50, the product name: Micro Acilyzer S-3, manufactured by ASTOM Corporation), water in an amount corresponding to 17% of the extract liquid was placed in a concentration chamber, and an electrodialysis treatment was performed until the electric conductivity in the desalting chamber reached equilibrium (2 millisiemens per centimeter (mS/cm)), and then, a concentrate liquid was collected. Further, this concentrate liquid was concentrated using an evaporator until the Brix reached 11.5. The temperature of the concentrate liquid having a Brix of 11.5 was increased to 90° C. to effect sterilization, followed by cooling to 50° C. or lower, whereby an electrodialysate was obtained.

Dextrin (manufactured by Cargill Japan) was added at a weight ratio of 60 with respect to 40 of the solid content of the electrodialysate having a Brix of 11.5 obtained above, and water was mixed therein to dissolve the components, and the resulting solution was powdered using a spray dryer (manufactured by Nihon Buchi). The powderization was performed under the same powderization condition as in Example 1(3). The obtained powder was named "electrodialysate dry powder".

When the electrodialysate dry powder was left at room temperature for 2 hours, the powder was partially liquified, and therefore, it was confirmed by visual observation that the electrodialysate dry powder deliquesced.

Example 6

Production of Fermented Food Product Containing Lactic Acid Bacteria (1)

A 15% powdered skim milk solution containing 4% glucose was used as a basal culture medium, and each of the tien-cha extract essence dry powders A and B produced in Example 5, and the tien-cha extract dry powder and the electrodialysate dry powder produced in Reference Example 2 was added to the basal culture medium in an amount of 0.012% in terms of dry powder which does not contain dextrin (0.1% in terms of concentrate liquid having a Brix of 11.5 before powderization). Into this culture medium, a starter of *Lactobacillus casei* YIT9029 was inoculated in an amount of 0.5% (initial cell count: 7.5×10$^6$ cfu/mL), and culturing was performed at 37° C. for 24 hours to obtain a culture of lactic acid bacteria, followed by cooling to 10° C. or lower, whereby a fermented milk was obtained. The pH and acidity of this fermented milk and the viable cell count and flavor therein were measured. The measurement methods of the respective items were performed in the same manner as in Example 2. The results are shown in Table 5.

TABLE 5

| Additive | pH of fermented milk | Acidity of fermented milk | Viable cell count in fermented milk (cfu/mL) | Flavor |
|---|---|---|---|---|
| Non | 5.42 | 4.2 | 4.4 × 10$^8$ | 5 |
| Tien-cha extract dry powder | 4.32 | 11.2 | 6.1 × 10$^9$ | 3 |
| Electrodialysate dry powder | 4.28 | 11.8 | 7.3 × 10$^9$ | 5 |
| Tien-cha extract essence dry powder A | 4.30 | 11.6 | 6.9 × 10$^9$ | 5 |
| Tien-cha extract essence dry powder B | 4.30 | 11.5 | 7.4 × 10$^9$ | 5 |

In the case where an additive was not present, the viable cell count in the fermented milk was low (less than 5.0×10$^8$ cfu/mL), and promotion of growth was not confirmed also from the pH and acidity.

On the other hand, in the case where each of the tien-cha extract dry powder, the electrodialysate dry powder, and the tien-cha extract essence dry powders A and B was added, the viable cell count was high, and an effect of promoting the growth was remarkably exhibited also from the pH and acidity.

Further, in the case where the tien-cha extract dry powder was used, the flavor of the fermented milk was poor, however, in the case where each of the electrodialysate dry powder, and the tien-cha extract essence dry powders A and B was used, an effect on the flavor was not observed.

Therefore, it was found that the tien-cha extract essence dry powders A and B have an effect of promoting the growth of *Lactobacillus casei* equally to the electrodialysate dry powder, and have no effect on the flavor of the fermented milk.

Example 7

Production of Fermented Food Product Containing Lactic Acid Bacteria (2)

A test was performed under the same condition as in Example 6 except that *Lactobacillus gasseri* YIT0192 was inoculated in an amount of 0.5% (initial cell count: 4.5×10$^6$ cfu/mL) in place of *Lactobacillus casei* YIT9029. The results are shown in Table 6.

TABLE 6

| Additive | pH of fermented milk | Acidity of fermented milk | Viable cell count in fermented milk (cfu/mL) | Flavor |
|---|---|---|---|---|
| Non | 5.84 | 2.6 | 7.4 × 10$^7$ | 5 |
| Tien-cha extract dry powder | 5.41 | 4.3 | 5.1 × 10$^8$ | 3 |
| Electrodialysate dry powder | 5.38 | 4.7 | 7.3 × 10$^8$ | 5 |
| Tien-cha extract essence dry powder A | 5.39 | 4.5 | 6.1 × 10$^8$ | 5 |
| Tien-cha extract essence dry powder B | 5.39 | 4.5 | 5.4 × 10$^8$ | 5 |

Similarly to the results of Example 6, in the case where an additive was not present, the viable cell count in the fermented milk was low (less than 5.0×10$^8$ cfu/mL), and promotion of growth was not confirmed also from the pH and acidity. However, in the case where each of the tien-cha extract dry powder, the electrodialysate dry powder, and the tien-cha extract essence dry powders A and B was added, the viable cell count was high, and an effect of promoting the growth was remarkably exhibited also from the pH and acidity.

Further, in the case where the tien-cha extract dry powder was used, the flavor of the fermented milk was poor, however, in the case where each of the electrodialysate dry powder, and the tien-cha extract essence dry powders A and B was used, an effect on the flavor was not observed.

Therefore, it was found that the tien-cha extract essence dry powders A and B have an effect of promoting the growth of not only *Lactobacillus casei*, but also *Lactobacillus gasseri* equally to the electrodialysate dry powder, and have no effect on the flavor of the fermented milk.

Example 8

Production of Fermented Food Product Containing *Bifidobacterium* Bacteria (1)

A 15% powdered skim milk solution was used as a basal culture medium, and each of the tien-cha extract essence dry powders A and B produced in Example 5, and the tien-cha extract dry powder and the electrodialysate dry powder produced in Reference Example 2 was added to the basal culture medium in an amount 0.012% in terms of dry powder which does not contain dextrin (0.1% in terms of concentrate liquid having a Brix of 11.5 before powderization). Into this culture medium, each of a starter of *Bifidobacterium breve* YIT12272 in an amount of 1% (initial cell count: $1.0 \times 10^7$ cfu/mL), a starter of *Lactococcus lactis* YIT2027 in an amount of 0.1% (initial cell count: $1.0 \times 10^6$ cfu/mL), and a starter of *Streptococcus thermophiles* YIT2021 in an amount of 0.1% (initial cell count: $1.2 \times 10^6$ cfu/mL) was inoculated, and culturing was performed at 35° C. until the pH reached 4.4. To 40 parts by weight of this culture having undergone homogenization at 15 MPa, 60 parts by weight of a 10% sucrose solution having undergone sterilization at 100° C. for 5 minutes was added, whereby a fermented milk was produced. The produced fermented milk was packed in a glass container, and the container was tightly sealed with a butyl stopper and stored at 10° C. under an anaerobic condition for 21 days. The viable cell count before and after storage was measured in the same manner as in Example 3. Further, the flavor after storage was evaluated in the same manner as in Example 2. In addition, from the viable cell count before and after storage, the viability was obtained in the same manner as in Example 3. These results are shown in Table 7.

TABLE 7

| Additive | Viable cell count at production (cfu/mL) | Viable cell count after storage (cfu/mL) | Viability (%) | Flavor |
|---|---|---|---|---|
| Non | $1.1 \times 10^9$ | $2.1 \times 10^8$ | 19 | 5 |
| Tien-cha extract dry powder | $1.3 \times 10^9$ | $4.5 \times 10^8$ | 35 | 3 |
| Electrodialysate dry powder | $1.2 \times 10^9$ | $4.2 \times 10^8$ | 35 | 5 |
| Tien-cha extract essence dry powder A | $1.3 \times 10^9$ | $4.3 \times 10^8$ | 33 | 5 |
| Tien-cha extract essence dry powder B | $1.2 \times 10^9$ | $3.9 \times 10^8$ | 33 | 5 |

*As the viable cell count and the viability, the values of Bifidobacterium breve YIT12272 are shown.

In the case where an additive was not present, the viability of *Bifidobacterium breve* was low.

On the other hand, in the case where each of the tien-cha extract dry powder, the electrodialysate dry powder, and the tien-cha extract essence dry powders A and B was added, the viability of *Bifidobacterium breve* was high, and an effect of improving the viability was remarkably exhibited.

Further, in the case where the tien-cha extract dry powder was used, the flavor of the fermented milk was poor, however, in the case where each of the electrodialysate dry powder, and the tien-cha extract essence dry powders A and B was used, an effect on the flavor was not observed.

Therefore, it was found that the tien-cha extract essence dry powders A and B have an effect of improving the viability of *Bifidobacterium breve* equally to the electrodialysate dry powder, and have no effect on the flavor of the fermented milk.

Example 9

Production of Fermented Food Product Containing *Bifidobacterium* Bacteria (2)

A test was performed under the same condition as in Example 8 except that each of a starter of *Bifidobacterium bifidum* YIT10347 in an amount of 2% (initial cell count: $2.2 \times 10^7$ cfu/mL) and a starter of *Streptococcus thermophiles* YIT2021 in an amount of 0.01% (initial cell count: $1.2 \times 10^5$ cfu/mL) was inoculated in place of the starter of *Bifidobacterium breve* YIT12272 in an amount of 1%, and the starters of *Lactococcus lactis* YIT2027 and *Streptococcus thermophiles* YIT2021 in an amount of 0.1%. The results are shown in Table 8.

TABLE 8

| Additive | Viable cell count at production (cfu/mL) | Viable cell count after storage (cfu/mL) | Viability (%) | Flavor |
|---|---|---|---|---|
| Non | $1.6 \times 10^8$ | $4.3 \times 10^7$ | 27 | 5 |
| Tien-cha extract dry powder | $1.8 \times 10^8$ | $6.7 \times 10^7$ | 37 | 3 |
| Electrodialysate dry powder | $1.7 \times 10^8$ | $7.0 \times 10^7$ | 41 | 5 |
| Tien-cha extract essence dry powder A | $1.8 \times 10^8$ | $7.1 \times 10^7$ | 39 | 5 |
| Tien-cha extract essence dry powder B | $1.7 \times 10^8$ | $6.9 \times 10^7$ | 41 | 5 |

*As the viable cell count and the viability, the values of Bifidobacterium bifidum YIT10347 are shown.

Similarly to the results of Example 8, in the case where an additive was not present, the viability of *Bifidobacterium bifidum* was low, however, in the case where each of the tien-cha extract dry powder, the electrodialysate dry powder, and the tien-cha extract essence dry powders A and B was added, the viability of *Bifidobacterium bifidum* was high, and an effect of improving the viability was remarkably exhibited.

Further, in the case where the tien-cha extract dry powder was used, the flavor of the fermented milk was poor, however, in the case where each of the electrodialysate dry powder, and the tien-cha extract essence dry powders A and B was used, an effect on the flavor was not observed.

Therefore, it was found that the tien-cha extract essence dry powders A and B have an effect of improving the viability of not only *Bifidobacterium breve*, but also *Bifidobacterium bifidum* equally to the electrodialysate dry powder, and have no effect on the flavor of the fermented milk.

INDUSTRIAL APPLICABILITY

The tien-cha extract essence of the present invention has no effect on flavor while maintaining the effects of the tien-cha extract of increasing the growth ability of lactic acid bacteria and the viability or the like of *bifidobacterium* bacteria, and also has an unprecedented effect of increasing the growth ability of *bifidobacterium* bacteria, and is easily produced and powdered.

Accordingly, the tien-cha extract essence of the present invention can be favorably used in the production of a fermented food product containing lactic acid bacteria or *bifidobacterium* bacteria.

The invention claimed is:

1. A tien-cha extract essence, which is a dry powder, obtained by subjecting leaves or stems of a *R. suavissimus* to solvent extraction with water under acidic condition at a pH of 4.0 or less, thereby obtaining an extract of tien-cha, wherein an inorganic salt is not added and electrodialysis is not used, and treating the tien-cha extract with an activated carbon, thereby obtaining the tien-cha extract essence,
   wherein the activated carbon is a chemically activated carbon, and wherein, when being left at room temperature for 2 hours, the tien-cha extract dry powder does not deliquesce.

2. The ties-cha extract essence according to claim 1, wherein an amount of the activated carbon in the activated carbon treatment is 0.035 wt % or more in terms of dry weight per degree Brix of the tien-cha extract.

3. A method for producing a tien-cha extract essence, which is a dry powder, the method comprising:
subjecting leaves or stems of a *R. suavissimus* to solvent extraction with water under acidic condition at a pH of 4.0 or less, thereby obtaining an extract of tien-cha, wherein an inorganic salt is not added and electrodialysis is not used,
treating the tien-cha extract with an activated carbon, thereby obtaining the tien-cha extract essence, and
drying the tien-cha extract essence to obtain a dry powder,
wherein the activated carbon is a chemically activated carbon, and
wherein, when being left at room temperature for 2 hours, the tien-cha extract dry powder does not deliquesce.

4. The method for producing a tien-cha extract essence according to claim 3, wherein an amount of the activated carbon in the activated carbon treatment is 0.035 wt % or more in terms of dry weight per degree Brix of the tien-cha extract.

5. A fermented food product, comprising a culture of lactic acid bacteria obtained by culturing the lactic acid bacteria in a culture medium in which the tien-cha extract essence according to claim 1 is blended wherein the tien-cha extract essence is a dry powder, and is obtained by subjecting leaves or stems of a *R. suavissimus* to solvent extraction with water under acidic condition at a pH of 4.0 or less, thereby obtaining an extract of tien-cha, wherein an inorganic salt is not added and electrodialysis is not used, and treating the tien-cha extract with an activated carbon, thereby obtaining the tien-cha extract essence,
wherein the activated carbon is a chemically activated carbon, and
wherein, when being left at room temperature for 2 hours, the tien-cha extract dry powder does not deliquesce.

6. A method for producing a fermented food product, comprising blending the tien-cha extract essence according to claim 1 in a culture medium, and then culturing lactic acid bacteria in the culture medium wherein the tien-cha extract essence is a dry powder, and is obtained by subjecting leaves or stems of a *R. suavissimus* to solvent extraction with water under acidic condition at a pH of 4.0 or less, thereby obtaining an extract of tien-cha, wherein an inorganic salt is not added and electrodialysis is not used, and treating the tien-cha extract with an activated carbon, thereby obtaining the tien-cha extract essence,
wherein the activated carbon is a chemically activated carbon, and
wherein, when being left at room temperature for 2 hours, the tien-cha extract dry powder does not deliquesce.

7. A fermented food product, comprising a culture of *bifidobacterium* bacteria obtained by culturing the *bifidobacterium* bacteria in a culture medium in which the tien-cha extract essence according to claim 1 is blended wherein the tien-cha extract essence is a dry powder, and is obtained by subjecting leaves or stems of a *R. suavissimus* to solvent extraction with water under acidic condition at a pH of 4.0 or less, thereby obtaining an extract of tien-cha, wherein an inorganic salt is not added and electrodialysis is not used, and treating the tien-cha extract with an activated carbon, thereby obtaining the tien-cha extract essence,
wherein the activated carbon is a chemically activated carbon, and
wherein, when being left at room temperature for 2 hours, the tien-cha extract dry powder does not deliquesce.

8. A method for producing a fermented food product, comprising blending the tien-cha extract essence according to claim 1 in a culture medium, and then culturing *bifidobacterium* bacteria in the culture medium wherein the tien-cha extract essence is a dry powder, and is obtained by subjecting leaves or stems of a *R. suavissimus* to solvent extraction with water under acidic condition at a pH of 4.0 or less, thereby obtaining an extract of tien-cha, wherein an inorganic salt is not added and electrodialysis is not used, and treating the tien-cha extract with an activated carbon, thereby obtaining the tien-cha extract essence,
wherein the activated carbon is a chemically activated carbon, and
wherein, when being left at room temperature for 2 hours, the tien-cha extract dry powder does not deliquesce.

9. A method for promoting the growth of lactic acid bacteria and/or *bifidobacterium* bacteria, comprising blending the tien-cha extract essence according to claim 1 in a culture medium, and then culturing the lactic acid bacteria and/or the *bifidobacterium* bacteria in the culture medium wherein the tien-cha extract essence is a dry powder, and is obtained by subjecting leaves or stems of a *R. suavissimus* to solvent extraction with water under acidic condition at a pH of 4.0 or less, thereby obtaining an extract of tien-cha, wherein an inorganic salt is not added and electrodialysis is not used, and treating the tien-cha extract with an activated carbon, thereby obtaining the tien-cha extract essence,
wherein the activated carbon is a chemically activated carbon, and
wherein, when being left at room temperature for 2 hours, the tien-cha extract dry powder does not deliquesce.

10. An agent for promoting the growth of lactic acid bacteria and/or *bifidobacterium* bacteria, comprising the tien-cha extract essence according to claim 1 as an active ingredient wherein the tien-cha extract essence is a dry powder, and is obtained by subjecting leaves or stems of a *R. suavissimus* to solvent extraction with water under acidic condition at a pH of 4.0 or less, thereby obtaining an extract of tien-cha, wherein an inorganic salt is not added and electrodialysis is not used, and treating the tien-cha extract with an activated carbon, thereby obtaining the tien-cha extract essence,
wherein the activated carbon is a chemically activated carbon, and
wherein, when being left at room temperature for 2 hours, the tien-cha extract dry powder does not deliquesce.

11. A method for improving the viability of *bifidobacterium* bacteria, comprising blending the tien-cha extract essence according to claim 1 in a culture medium, and then culturing the *bifidobacterium* bacteria in the culture medium wherein the tien-cha extract essence is a dry powder, and is obtained by subjecting leaves or stems of a *R. suavissimus* to solvent extraction with water under acidic condition at a pH of 4.0 or less, thereby obtaining an extract of tien-cha, wherein an inorganic salt is not added and electrodialysis is not used, and treating the tien-cha extract with an activated carbon, thereby obtaining the tien-cha extract essence,
wherein the activated carbon is a chemically activated carbon, and
wherein, when being left at room temperature for 2 hours, the tien-cha extract dry powder does not deliquesce.

12. An agent for improving the viability of *bifidobacterium* bacteria, comprising the tien-cha extract essence according to claim 1 as an active ingredient wherein the tien-cha extract essence is a dry powder, and is obtained by subjecting leaves or stems of a *R. suavissimus* to solvent extraction with water under acidic condition at a pH of 4.0 or less, thereby obtaining an extract of tien-cha, wherein an inorganic salt is not added and electrodialysis is not used, and treating the tien-cha extract with an activated carbon, thereby obtaining the tien-cha extract essence, wherein the activated carbon is a chemically activated carbon, and wherein, when being left at room temperature for 2 hours, the tien-cha extract dry powder does not deliquesce.

13. A method for improving flavor of a tien-cha extract essence, the method comprising:

subjecting leaves or stems of a *R. suavissimus* to solvent extraction with water under acidic condition at a pH of 4.0 or less, thereby obtaining an extract of tien-cha, wherein an inorganic salt is not added and electrodialysis is not used, and treating the tien-cha extract with an activated carbon, thereby obtaining the tien-cha extract essence, wherein the activated carbon is a chemically activated carbon, thereby improving the flavor of the tien-cha extract essence compared to flavor of a tien-cha extract essence obtained by using electrodialysis and an inorganic salt.

14. The tien-cha extract essence of claim 1, wherein after the treating of the tien-cha extract with the activated carbon, a diatomaceous earth filtration is performed to obtain the tien-cha extract essence.

15. The method of claim 3, further comprising, after the treating of the tien-cha extract with the activated carbon, conducting a diatomaceous earth filtration.

16. The method of claim 13, further comprising, after the treating of the tien-cha extract with the activated carbon, conducting a diatomaceous earth filtration.

\* \* \* \* \*